(12) United States Patent
Hakim

(10) Patent No.: US 10,058,503 B2
(45) Date of Patent: *Aug. 28, 2018

(54) DAILY FACE CREAM

(71) Applicant: Noha N. Hakim, Easton, PA (US)

(72) Inventor: Noha N. Hakim, Easton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,948

(22) Filed: Feb. 9, 2018

(65) Prior Publication Data

US 2018/0207088 A1    Jul. 26, 2018

Related U.S. Application Data

(63) Continuation-in-part of application No. 15/159,482, filed on May 19, 2016, now Pat. No. 9,949,920.

(51) Int. Cl.

| A61K 8/02 | (2006.01) |
|---|---|
| A61K 8/9794 | (2017.01) |
| A61K 8/9789 | (2017.01) |
| A61K 8/92 | (2006.01) |
| A61K 8/20 | (2006.01) |
| A61K 8/73 | (2006.01) |
| A61K 8/64 | (2006.01) |
| A61Q 19/00 | (2006.01) |
| A45D 40/00 | (2006.01) |
| A61K 8/36 | (2006.01) |

(52) U.S. Cl.
CPC ........ *A61K 8/9794* (2017.08); *A45D 40/0068* (2013.01); *A61K 8/20* (2013.01); *A61K 8/36* (2013.01); *A61K 8/645* (2013.01); *A61K 8/73* (2013.01); *A61K 8/922* (2013.01); *A61K 8/9789* (2017.08); *A61Q 19/007* (2013.01); *A61K 2800/87* (2013.01)

(58) Field of Classification Search
CPC ........ A61K 2300/00; A61K 8/34; A61K 8/97; A61K 36/67; A61K 36/81; A61K 2800/524; A61K 2800/596; A61K 31/4155; A61K 8/20; A61K 8/36; A61K 8/375; A61K 8/732; A61K 8/92; A61K 8/922; A61K 8/99; A61K 9/0014; A61K 2800/31; A61K 2800/782; A61K 31/11; A61K 31/16; A61K 47/22; A61K 8/0212; A61K 8/0229

See application file for complete search history.

(56) References Cited

U.S. PATENT DOCUMENTS

| | | | | |
|---|---|---|---|---|
| 4,505,902 | A * | 3/1985 | Millard | A61K 8/922 424/735 |
| 4,943,432 | A * | 7/1990 | Biener | A61K 8/19 424/647 |
| 5,705,172 | A * | 1/1998 | Efron | A61F 7/02 424/402 |
| 5,866,145 | A * | 2/1999 | Stavroff | A61K 8/03 424/401 |
| 6,582,709 | B1 * | 6/2003 | Maor | A61K 8/27 424/401 |
| 6,723,309 | B1 * | 4/2004 | Deane | A61K 8/416 424/70.1 |
| 8,486,463 | B1 * | 7/2013 | Brieva | A61K 8/97 424/725 |
| 2006/0134238 | A1 * | 6/2006 | Dnyaneshwar | A61K 36/886 424/744 |
| 2008/0175928 | A1 * | 7/2008 | Jochim | A61K 8/0212 424/727 |
| 2008/0286390 | A1 * | 11/2008 | Tanyi | A61K 8/922 424/744 |
| 2011/0212184 | A1 * | 9/2011 | Samelson | A61K 8/044 424/537 |

* cited by examiner

*Primary Examiner* — Nannette Holloman
(74) *Attorney, Agent, or Firm* — Gary P. Topolosky

(57) ABSTRACT

This invention is a natural face cream/lotion that exploits the benefits of Dead Sea salt for helping moisturize the skin of a human face. The lotion consists of natural ingredients such as organic aloe vera juice, shea butter, preferably unrefined, emulsified wax, Dead Sea salt, hydrolyzed wheat protein, essential oils (particularly lavender, rosehip seed oil and carrot seed oil), apple cider vinegar, and xanthan gum. They are included with a preservative made from leuconostoc/radish root ferment filtrate and phenoxyethanol.

10 Claims, No Drawings

DAILY FACE CREAM

CROSS REFERENCE TO RELATED APPLICATION

This application is a continuation-in-part of commonly-owned U.S. application Ser. No. 15/159,482, filed on May 19, 2016, the disclosure of which is fully incorporated herein.

BACKGROUND

The skin for the human body secretes slightly acidic natural oil called sebum to protect it from becoming too dry. Dry skin is a condition, not a disease, and can be caused by using harsh soaps, itchy clothing, unsuitable body moisturizers, hot and cold weather, hard water and diet. Also medications for such medical conditions as diabetes, psoriasis, hypothyroidism, and malnutrition may cause severe dry skin. See generally, http://www.webmd.boots.com/healthy-skin/guide/causes-dry-skin.

Some signs of dry skin on the human body include itching, flaking, skin redness and cracks, skin tightness after shower. See, http://www.mayoclinic.org/diseases-conditions/dry-skin/basics/symptoms/con-20030009.

The lotion/cream of this invention is especially noted for use with the human body, particularly the face. It is meant to be applied as a daily face cream for moisturizing AND skin softening.

Field of the Invention

Although dry patches on the face can be caused by medications, hormone imbalances, or skin conditions, dry patches are commonly caused by incorrect skincare and extreme weather conditions. Some facial soaps and cleansers can actually be too harsh for the sensitive skin on the face.

This invention relates to face lotions. Particularly, it relates to lotions for helping the skin of one's face avoid dehydration, dryness and to reduce other skin symptoms including itching, flaking or cracking. It serves as both a moisturizer and a skin softener. Preferred composition will be sold under the SeaLand Cosmetics™ brand.

The SeaLand Cosmetics Daily Face Cream is a unique combination of salt from the Dead Sea and the earth's natural ingredients such as organic aloe vera, shea butter, emulsified wax, hydrolyzed wheat protein, apple cider vinegar and xanthun gum along with several, specially selected pure essential oils. This particular formulation will help hydrate, moisturize and soften the human face.

To assure safety of the product, SeaLand Cosmetics uses in this face cream/lotion a combination of: (i) a natural preservative leuconostoc/radish root ferment filtrate (one version of which is sold under the trademark, Leucidal®); and (ii) phenoxyethanol which is a nature identical chemical that can be found in green tea and produced by treating phenol with ethylene oxide in an alkaline medium that reacts to form a pH balanced ingredient. This synthetically produced commercial ingredient does not release formaldehyde or cause health risks thus assuring safety of the product. One commercial product is Optiphen® Plus and is used with <1.0% in the face cream:lotion formulation of this invention. Should Optiphen® no longer be commercially available, substantially equivalent alternatives may be substituted therefor.

Related Art

Dead Sea salt, as removed from waters from the Dead Sea water, is a known component for various preferred end uses. Biener U.S. Pat. No. 4,943,432 added such salts to magnesium halide, several alkaline earth metal salts and other cations as part of a composition for treating psoriasis.

Stravroff et al. U.S. Pat. No. 5,866,145 mixed Dead Sea salts with some silicone oils and fragrances to serve as a moisturizing body "polisher".

Maor et al. U.S. Pat. No. 6,582,709 discloses a pharmaceutical cream composition for the treatment of skin disorders, said composition including about 1-6 wt. % Dead Sea mud as an active ingredient.

Lucenta U.S. Published Application No. 20110229419 mixed Dead Sea salt with sodium chloride for the prevention and healing of canker sores.

And Samuelson et al. U.S. Pat. No. 9,050,273 discloses using ultra fine Dead Sea mineral compounds in compositions for use in bath and body products.

The Dead Sea is one of the most saline lakes in the world. It lies between the hills of Judaea to the west and the Trans-Jordanian plateaus to the east. The Jordan River flows from the north into the Dead Sea. About 2.5 million years ago, heavy stream flow into the lake deposited thick sediments containing shale, clay, sandstone, rock salt, and gypsum. After this, strata of clay, marl, soft chalk, and gypsum fell upon layers of sand and gravel.

Having no outlet, the Dead Sea is a "terminal lake" meaning that it loses huge amounts of water by evaporation in the hot dry air. The water has evaporated faster than it has been replenished by precipitation over the last 10,000 years. That results in the lake gradually shrinking to its present form. Because of this, bare deposits cover the Dead Sea valley to a thickness of 1 to 4 miles (1.6 to 6.4 km). This water evaporation has also resulted in high concentrations of salts and minerals in a unique composition particularly rich in magnesium, sodium, potassium, calcium, bromide and various other minor anions such as, e.g., sulfate.

The concentration of salt increases as one descends toward the bottom of the Dead Sea. Down to 130 feet (40 m), the temperature varies from 66 to 98° F. (19 to 37° C.), and the salinity is slightly less than 300 parts per thousand. At this depth, the water is particularly rich in sulfates and bicarbonates. There is a transition zone located between 130 and 330 ft. (40 and 100 m). The lower waters below 330 ft. (1.00 m) have a uniform temperature of about 72° F. (22° C.) and a higher degree of salinity (approximately 332 parts per thousand). This lower water contains hydrogen sulfide along with strong concentrations of magnesium, potassium, chlorine, and bromine. Below that level, the deepest waters are saturated with sodium chloride that precipitates to the bottom.

The lower waters of the Dead Sea are fossilized; they remain permanently on the bottom because they are very salty and dense. The upper waxers date from a few centuries A.D.

The Dead Sea's mineral composition differs from that of ocean water; the salt in most oceans is approximately 85% sodium chloride while Dead Sea salt is only 12-18% sodium chloride. An analysis of major ion concentrations in the water of the Dead Sea gave the following results. (Reference 1, below)

The major ions in Dead Sea water are:

| Ion | Concentration (mg/L) |
| --- | --- |
| Chloride and Bromide | 230,400 |
| Magnesium | 45,900 |
| Sodium | 36,600 |

-continued

| Ion | Concentration (mg/L) |
|---|---|
| Calcium | 17,600 |
| Potassium | 7,800 |

The Dead Sea's overall salt concentration is 340 g/L according to Reference 1. One study concluded that the high concentration of Mg in Dead Sea salt made it instrumental in improving skin hydration and reducing inflammation (Reference 2). According to Reference 3, the high concentration of bromide and magnesium in Dead Sea salt can cleanse and detoxify the skin and body. References 4 and 5 both address bathing in a Mg-rich, Dead Sea salt solution.

REFERENCES

1, Kuehl B L, Fyfe K S, Shear N H (March 2003). "Cutaneous cleansers". Skin Therapy Lett 8 (3): 1-4. *PMID* 12858234.

2, Pierce J D Jr, Zeng X N, Aronov E V, Preti G, Wysocki C J (August 1995). "Cross-adaptation of sweaty-smelling 3-methyl-2-hexenoic acid by a structurally similar, pleasant-smelling odorant". Chem Senses 20 (4): 401-11. *doi:* 10.1093/*chemse/*20.4.401. *PMID* 8590025.

3, Ma'or, Zeev et al. "*Antimicrobial properties of Dead Sea black mineral mud*", International Journal of Dermatology, May 2006, Retrieved on 2008 Apr. 13.

4, Proksch, Ehrhardt M D, PhD et al. "*Bathing in a magnesium-rich Dead Sea salt solution improves skin barrier function, enhances skin hydration, and reduces inflammation in atopic dry skin*", International Journal of Dermatology, February 2005, Retrieved 2008 Apr. 13.

5, Ehrhardt, Proksch; Nissen, H P; Bremgartner, M; Urquhart, C. "Bathing in a magnesium-rich Dead Sea salt solution: follow-on review". International Journal of Dermatology 46 (2): 177-179. *doi:* 10.1111/j.1365-4632.2005.02079.x. PMID 15689218.

SUMMARY OF THE INVENTION

A first object of the invention is to create a natural formulation that contains about 4% Dead Sea salt for humans use to improve hydration of the face and soften the skin thereon.

The second object of this invention is to use Shea Butter and avoid adding any kind of vegetable oils. The pure unrefined Shea butter is an off-white fatty substance obtained from the nuts of the shea tree from West Africa. It is perfect for face skin because it is extremely moisturizing and very hydrating, when applied to the skin; it provides immediate softness and smoothness. Shea butter is non-comedogenic (doesn't clog skin pores), rich of vitamin A and E and it helps to reduce inflammation according to "The Journal of Oleo Science Reference: https://www.ncbi.nlm.nih.gov/pubmed/20484832".

This natural formulation of a daily cream/lotion for the human face also includes natural ingredients as organic aloe vera juice, hydrolyzed wheat protein, Essential oils (particularly lavender, rosehip seed oil and carrot seed oil), Emulsifying Wax, apple cider vinegar, and xanthan gum. They are combined with a preservative made from leuconostoc/radish root ferment filtrate and phenoxyethanol.

Note that this Vegan face cream/lotion product does not contain ingredients like triclosan, phthalates, or soy.

DESCRIPTION OF PREFERRED EMBODIMENTS

Ideally, the composition of this human face cream/lotion includes the following in addition to its main novel ingredient of Dead Sea salt.

Aloe Vera juice: It is used instead of water as a diluent; the juice is made of the whole Aloe Vera leaves to include inner gel that soothes the skin and serves as an anti-inflammatory. The herb can be an effective moisturizing agent and has antimicrobial properties against many common bacteria and fungi.

Unrefined Shea Butter: The concentration of natural vitamins (A, E and F) and fatty acids such as oleic, stearic, palmitic and linolenic acids in Shea butter help to moisturize skin and provides the nutrients necessary for collagen production. See, generally, http://www.ncbi.nlm.nih.gov/pubmed/20484832.

NF emulsifying wax (vegetable based): It is used to form emulsion between water and oil ingredients by attracting them to different portions of its structure (hydrophilic for water molecules and hydrophobic for oil molecules).

Hydrolyzed Wheat Protein: Hydrolyzed wheat protein is also called phyto peptides. This type of protein helps to retain water and improve skin moisture.

Essential oils:
Lavender—Lavender is a member of the mint family. The oil from lavender is one of the most well-known essential oils in aromatherapy. It is most commonly known for its antibacterial and anti-inflammatory properties.
Rosehip seed oil—Rose hip oil is classified as a dry oil which quickly absorbs into the skin offering several benefits with its primary constituents of Vitamins E, C, A and B-carotene.
Carrot seed oil—Carrot seed oil primarily contains the well-known pigment carotene and is high in antioxidants. It has the ability to rejuvenate the look and feel of the face skin.
Apple cider vinegar: It keeps the pH of this face cream/lotion on the acidic side; plus it has antiseptic, anti-fungal and anti-bacterial properties.

Preservatives: One preferred set of preservatives for use in this product consists of:
(i) 1.4% natural preservative called Leucidal® liquid, it is a product derived from radishes fermented with leuconostoc kimchii, a lactic acid bacteria that has traditionally been used to make kimchi, this product consists of an isolated peptide that is secreted from the bacteria during the fermentation process that has been shown to have antimicrobial benefits. Leucidal® liquid is accepted by ECOcert as an ingredient in certified organic cosmetics. and
(ii) 0.6% phenoxyethanol. Though the latter is not natural, it is the only synthetic preservative which: doesn't release formaldehyde, works well with formulas having a pH less than 6 and which causes the least skin irritation. One representative off-the-shelf preservative is a product called Optiphen® Plus, the listed ingredients of which include phenoxyethanol, caprylyl glycol and sorbic acid.

The xanthan gum is a purposefully additive for lotion thickening.

EXAMPLE

A typical sales quantity of this daily face cream lotion would be packaged in 4 oz. container. A main formula for that lotion according to this invention consists of:

Organic Aloe Vera: 74.5%
Unrefined Shea Butter: 10%
NF Emulsifying Wax (Vegetable Based): 5% (Note that NF is short for National Formulary, meaning that this emulsifying wax conforms to the specifications of the NF).
Dead Sea Salt: 4%
Hydrolyzed Wheat Protein: 2%
Essential Oils (Lavender, Rosehip seed oil, Carrot seed oil): 1%
Leuconostoc/radish root ferment filtrate: 1.2%
Apple Cider Vinegar: 1%
Phenoxyethanol (Optiphen Plus): 0.8%
Xanthan gum: 0.5%

It should be noted that the organic aloe vera juice used in this formula contains natural preservatives, particularly potassium sorbate and citric acid.

The aforementioned ingredients are mixed altogether and fill in container can be glass or plastic of 2 or 4 oz. sizes with a regular lid. Directions for use of this invention are to apply directly to the user's clean face. Massage it into the skin of the face, applying it daily, as much as needed.

If the user suspects an allergic reaction, he/she should discontinue further uses and consult a physician.

While the invention has been described with a certain degree of particularity, it is manifest that many changes may be made in the arrangement of components without departing from the spirit and scope of this disclosure. It is understood that the invention is not limited to the embodiments set forth herein for purposes of exemplification, but is to be limited only by the scope of the attached claim or claims.

What is claimed is:

1. A lotion for use as a daily face cream, said lotion comprising:
   (a) about 70-80% by weight of the composition organic aloe vera juice,
   (b) about 7-13% by weight of the composition shea butter,
   (c) about 3-7% by weight of the composition emulsified wax,
   (d) about 3-5% by weight of the composition Dead Sea salt,
   (e) about 1-3% by weight of the composition hydrolyzed wheat protein,
   (f) about 0.5-2% by weight of the composition essential oils,
   (g) about 0.5-1.5% by weight of the composition apple cider vinegar, and
   (h) about 0.2-0.7% by weight of the composition xanthan gum.

2. The face cream/lotion of claim 1, wherein said composition further includes:
   (i) about 1.6-2.4% by weight of the composition of a preservative.

3. The face cream/lotion of claim 2 wherein the preservative consists essentially of:
   (i) about 1-1.5% by weight of the composition leuconostoc/radish root ferment filtrate; and
   (ii) about 0.6-1% by weight of the composition phenoxyethanol.

4. The face cream/lotion of claim 3 wherein the preservative consists essentially of:
   (i) about 1.2% by weight of the composition leuconostoc/radish root ferment filtrate; and
   (ii) about 0.8% by weight of the composition phenoxyethanol.

5. The face cream/lotion of claim 1 wherein the essential oils include lavender, rosehip seed oil and carrot seed oil.

6. The face cream lotion of claim 1 wherein said composition comprises:
   (a) about 74.5% by weight of the composition organic aloe vera juice,
   (b) about 10% by weight of the composition unrefined shea butter,
   (c) about 5% by weight of the composition emulsified wax,
   (d) about 4% by weight of the composition Dead Sea salt,
   (e) about 2% by weight of the composition hydrolyzed wheat protein,
   (f) about 1% by weight of the composition essential oils including lavender, rosehip seed oil and carrot seed oil,
   (g) about 1% by weight of the composition apple cider vinegar, and
   (h) about 0.5% by weight of the composition xanthan gum.

7. The face cream lotion of claim 1, which is made in quantities of about 500 mL +/−50 mL, packed in individual containers and stored at room temperature.

8. A method for helping moisturize and soften skin of a human face, said method comprising:
   (i) providing a face cream comprising:
      (a) about 70-80% by weight of the composition organic aloe vera juice,
      (b) about 713% by weight of the composition shea butter,
      (c) about 37% by weight of the composition emulsified wax,
      (d) about 35% by weight of the composition Dead Sea salt,
      (e) about 13% by weight of the composition hydrolyzed wheat protein,
      (f) about 0.52% by weight of the composition essential oils,
      (g) about 0.5-1.5% by weight of the composition apple cider vinegar,
      (h) about 0.2-0.7% by weight of the composition xanthan gum, and
      (i) about 1.6-2.4% by weight of the composition of a preservative,
   (ii) supplying the face cream in a jar for applying to the human face; and
   (iii) applying the face cream from the jar to the human face.

9. The method of claim 8 wherein the preservative in the face cream consists essentially of:
   (i) about 1-1.8% by weight of the composition leuconostoc/radish root ferment filtrate; and
   (ii) about 0.4-1% by weight of the composition phenoxethanol.

10. The method of claim 8 wherein the blend of pure essential oils include lavender, rosehip seed oil and carrot seed oil.

* * * * *